United States Patent [19]

Ohno et al.

[11] 4,347,138
[45] Aug. 31, 1982

[54] METHOD OF SEPARATING SERUM ALBUMIN AND GAMMA-GLOBULIN FROM EACH OTHER

[75] Inventors: Shotaro Ohno; Kenji Koyama, both of Tokuyama; Mitsutoshi Fukuda, Shin Nanyo, all of Japan

[73] Assignee: Toyo Soda Manufacturing Co., Ltd., Yamaguchi, Japan

[21] Appl. No.: 212,746

[22] Filed: Dec. 3, 1980

[30] Foreign Application Priority Data

Dec. 10, 1979 [JP] Japan .................. 54-159131

[51] Int. Cl.³ .............................................. B01D 13/00
[52] U.S. Cl. .................................... 210/639; 210/651; 210/927
[58] Field of Search ............... 210/639, 650, 651, 927; 422/101

[56] References Cited

U.S. PATENT DOCUMENTS 3,615,024 10/1971 Michaels ............................. 210/490
4,222,870 9/1980 Sternberg et al. ................. 210/639

OTHER PUBLICATIONS

Blatt, W. F. et al., "Solute Polarization and Cake Formation in Membrane Ultrafiltration . . . ", in Membrane Science and Technology, Plenum Press, N.Y. 1970.
Blatt, W. F., "Membrane Partition Chromatography . . . ", J. Agr. Food Chem., vol. 19, No. 4, 1971, pp. 589–594.
Porter, M. C. et al., "Membrane Ultrafiltration", Chemical Technology, Jan. 1971.

Primary Examiner—Charles N. Hart
Assistant Examiner—David R. Sadowski
Attorney, Agent, or Firm—Cushman, Darby & Cushman

[57] ABSTRACT

Serum albumin and a serum γ-globulin are separated by filtration from each other in a solution of a mixture thereof by using an ultrafiltration membrane. The ultrafiltration membrane has a fractionation molecular weight of about 100,000. The total protein concentration and salt concentration in the mixture solution to be forced through the membrane are adjusted to not more than 4 g/dl and not more than 0.6 mole/l, respectively. Also, the pH of the solution is adjusted to a value of from about 3.8 to about 4.7.

3 Claims, 5 Drawing Figures

METHOD OF SEPARATING SERUM ALBUMIN AND GAMMA-GLOBULIN FROM EACH OTHER

BACKGROUND OF THE INVENTION

1. Field of the Invention

This invention relates to a method of separating albumin and a γ-globulin contained in blood serum. More particularly, it relates to a method of separating albumin and a serum γ-globulin from each other in a solution containing these serum proteins by filtering the solution with a semipermeable membrane.

2. Description of the Prior Art

Blood serum proteins of a human or other mammals are mainly composed of albumin having a molecular weight of about $7 \times 10^4$ and a γ-globulin having a molecular weight of about $1.6 \times 10^5$. These two proteins occupy at least about 70% of the total blood serum proteins. These proteins are fractionated, and for example, human blood serum protein fractions have been used for medical purposes. As methods for the fractionation of blood serum proteins, there have been heretofore adopted a salting-out method, a precipitation method using cold ethanol or polyethylene glycol, and there has recently been developed a gel filtration chromatography method and an ion exchange chromatography method. In the former two methods, undesirable modification of the blood serum proteins is liable to occur and the separating operation is very complicated. The latter two methods are not suitable for large-scale fractionation.

A semipermeable membrane can be advantageously employed for the separation of molecules greatly differing from each other in molecular weight, i.e., the separation of macromolecular substances from low molecular weight substances. Thus, a semipermeable membrane has heretofore been used for dialysis.

An asymmetric membrane having a relatively good capacity has recently been developed, and semipermeable membranes of this type have widely been employed by using a pressure as the driving force as in ordinary filtration. According to this method, however, separation of macromolecules from each other is ordinarily considered difficult, although the molecular weight differs to an appreciable extent. It is construed that this difficulty is due to a broad pore size distribution of the membrane. However, the permeability of molecules through the membrane greatly varies depending not only upon the molecular weight, but also upon other ambient factors, for example, the co-existence of other proteins and the hydrogen ion concentration or salt concentration in the buffered solution. It has been reported, for example, that human γ-globulins and albumin are separated from each other by using a cellulose acetate membrane [see Oss et al., Membrane Science and Technology, page 146 (1970), edited by J. E. Flinn]. According to this method, separation of albumin and the γ-globulins in an artifically mixed solution containing pure albumin and γ-globulins including a dimer thereof has been successful, but separation of these proteins in a solution lacking the co-existence of the γ-globulin dimer or a solution containing whole blood serum has been impossible.

SUMMARY OF THE INVENTION

It is a primary object of the present invention to provide a method of separating serum albumin and a γ-globulin from each other by using a semipermeable membrane, whereby albumin and a γ-globulin can be separated at an enhanced efficiency.

Another object of this invention is to provide a method of separating serum albumin and a serum γ-globulin from each other in a solution system lacking the co-existence of a γ-globulin dimer by using a semipermeable membrane.

A further object of the present invention is to provide a method of separating serum albumin and a serum γ-globulin from each other in a solution containing whole blood serum by using a semipermeable membrane.

A still further object of the present invention is to provide a method of separating serum alubumin and a serum γ-globulin from each other in a solution containing these serum proteins at a high concentration by using a semipermeable membrane.

Other objects and advantages of the present invention will be apparent from the following description.

In accordance with the present invention, there is provided a method of separating serum albumin and a serum γ-globulin from each other in a solution of a mixture thereof by using a semipermeable membrane, wherein ultrafiltration is carried out by using as the semipermeable membrane an ultrafiltration membrane having a cut off molecular weight of about 100,000 while adjusting the total protein concentration and salt concentration in the mixture solution to not more than 4 g/dl and not more than 0.6 mole/l, respectively, and also adjusting the pH of the solution to a value of from about 3.8 to about 4.7.

DESCRIPTION OF THE PREFERRED EMBODIMENTS

Figure 1:
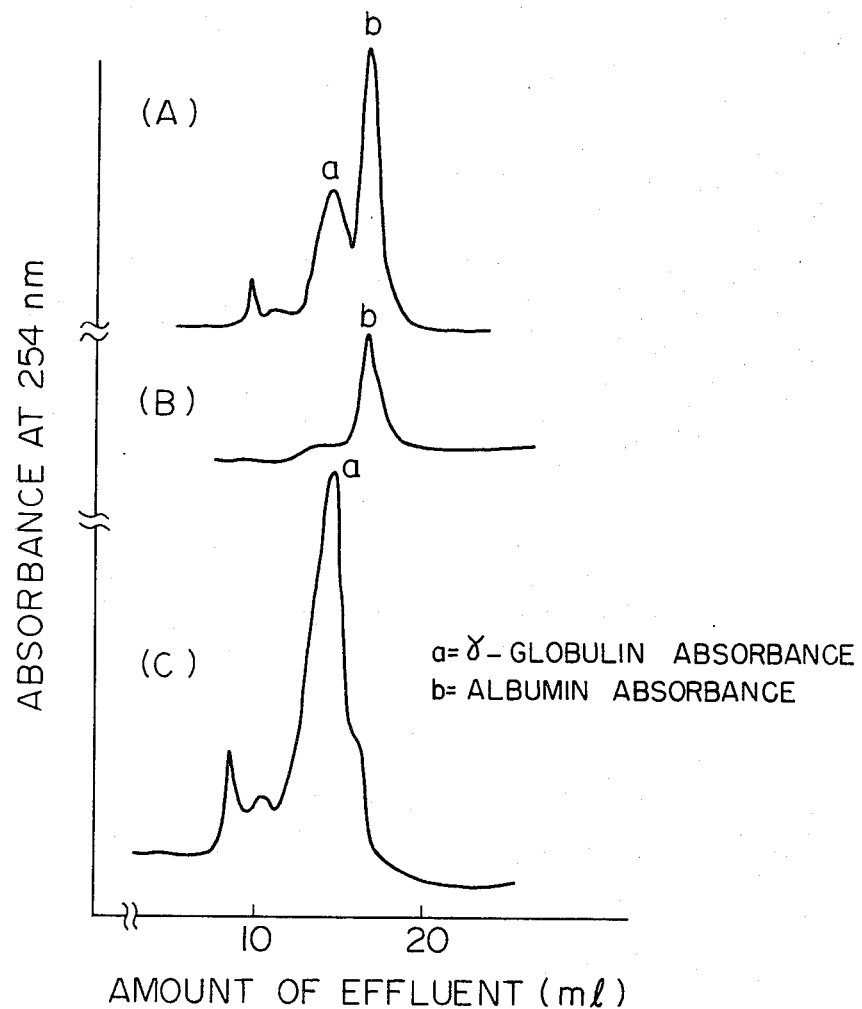
FIG. 1 shows chromatograms obtained by the liqud chromatography of a blood serum protein solution (A) used in one embodiment of the present invention and the protein solutions (B) and (C) fractionated from the blood serum protein solution according to the present invention.

A membrane composed of an aromatic polyether sulfone having recurring units represented by the following formula:

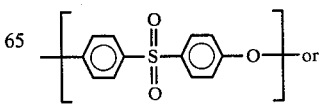

-continued

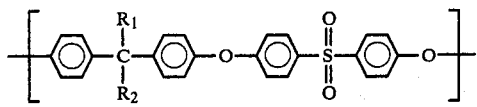

wherein $R_1$ and $R_2$ each stand for a hydrogen atom or an alkyl group having 1 to 2 carbon atoms, is especially preferred as the semipermeable membrane that is used in the present invention, and this membrane has a cut off molecular weight of about 100,000.

The cut off molecular weight of semipermeable membranes vary depending upon the shape and configuration of the molecule to be fractionated and the atmosphere where the molecule is placed, and therefore, the cut off molecular weight of the semipermeable membranes cannot always be precisely determined. By the term "semipermeable membrane having a cut off molecular weight of about 100,000" used herein is meant a semipermeable membrane capable of fractionating spherical molecules, such as proteins, having a molecular weight of from about 50,000 or about 60,000 to about 140,000 or about 150,000, as in the case of commercially available membranes having a nominal cut off molecular weight of about 100,000.

The thickness of the semipermeable membrane used in the present invention is not critical, but may usually be within a range of about 400 microns as in a conventional case.

The degree of polymerization of the aromatic polyether sulfone used for the preparation of the semipermeable membrane of the present invention is not critical, but may usually be within a range of about 500 to about 10,000 as in the case of using conventional aromatic polyether sulfone semipermeable membranes.

In the method of the present invention, membranes composed of a material other than the above-mentioned aromatic polyether sulfone can be used, but such membranes have defects when compared with the aromatic polyether sulfone membrane in the separation efficiency and are also defective in that clogging is liable to occur. Accordingly, it is preferable that a semipermeable membrane composed of the above-mentioned aromatic polyether sulfone be used.

In the method of the present invention, the filtration can be carried out as in the case of conventional semipermeable membrane filtration, for example, at a flow rate of about 0.1 to about 20 l/m² hr, which is not limitative in any way. The filtration pressure may preferably be in the range of from 0.1 to 5 kg/cm².

In the method of the present invention, the total protein concentration in the solution containing serum albumin and a γ-globulin to be separated is adjusted to not more than about 4 g/dl. If the total protein concentration exceeds this critical level, clogging of the membrane is often caused and separation becomes difficult.

The pH of the blood serum protein mixture solution is adjusted to a value of from about 3.8 to about 4.7, preferably 3.9 to 4.3. If the pH value exceeds about 4.7, the permeation of albumin is drastically reduced and separation cannot be carried out at a high efficiency. When the pH value of the solution is lower than about 3.8, there is a fear of modification of albumin. Furthermore, the salt concentration in the solution is adjusted to not more than about 0.6 mole/l. If the salt concentration exceeds this critical level, separation cannot be performed. The lower the salt concentration, the better the results obtained, in so far as proteins are present in a dissolved state in the solution. Ordinarily, the salt concentration may be at least 0.001 mole/l.

As the salts contained in the solution, there can be mentioned physiologically acceptable salts such as sodium chloride and salts inherently contained in the serum.

Various blood serum protein solutions containing albumin and γ-globulin can be used in the method of the present invention, and the states of the solutions are not particularly critical. For example, a solution prepared by diluting the total blood serum with pure water or a buffer solution and other solutions containing albumin and γ-globulin can be used in the present invention. Furthermore, not only the human blood serum but also sera of bovine, equine and swine can be used for separation according to the method of the present invention.

According to the present invention, separation of albumin and γ-globulin in the whole blood serum from each other or from other fractions, which has been impossible according to the conventional techniques, can be accomplished very easily. Furthermore, in the method of the present invention, the presence of a dimer of γ-globulin is not indispensable for the separation of albumin and γ-globulin. Moreover, the method of the present invention is advantageous over conventional methods of fractionation of blood serum proteins because the operation is very simple and the separation precision is very high, and therefore, the method of the present invention is suitable for large-scale separation. If the permeation conditions are appropriately adjusted, serum albumin and a γ-globulin, each having a desired purity, can be obtained in the form of solutions having a desired concentration, and if desired, in a continuous manner.

DETAILED DESCRIPTION OF THE DRAWINGS

As described in Examle 1, the chromatograms (A), (B) and (C) illustrated in FIG. 1 were obtained by the liquid chromatography of (i) a bovine blood serum solution, (ii) a filtrate obtained by the ultrafiltration of the solution (i), and (iii) a retenate obtained by the ultrafiltration of the solution (i), respectively. In these chromatograms, the peaks a and b indicate the absorbance of gamma-globulin and albumin, respectively, as measured at a wavelength of 254 nm.

Figure 2:
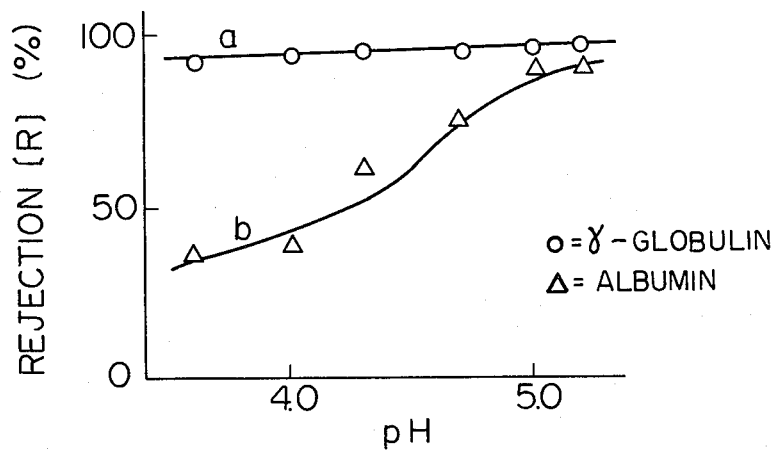
FIGS. 2 and 3 are diagrams illustrating influences of the hydrogen ion concentration and salt concentration in a blood serum protein solution, respectively, on fractionation of the blood serum protein solution.
Figure 3:
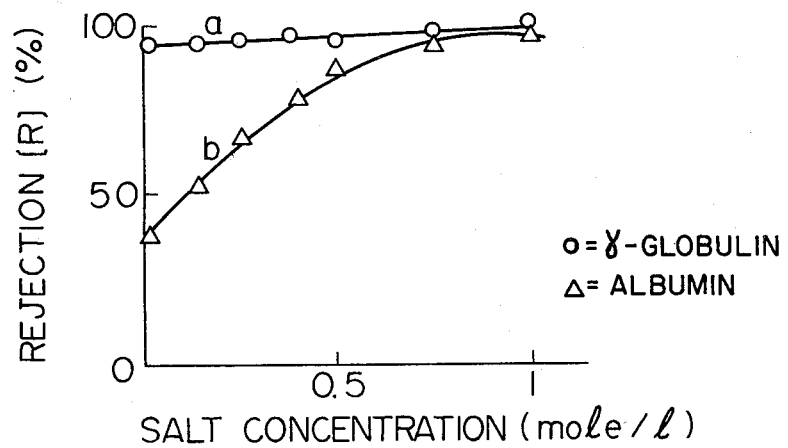

As described in Example 2, FIG. 2 illustrates a relationship of the salt concentration of the same bovine blood serum solution as used in Example 1 with the permeability of the membrane. FIG. 3 illustrates a relationship of the pH value of the same bovine blood serum solution as used in Example 1 with the permeability of the membrane. In the graphs of FIGS. 2 and 3, curves a (-o-) and b (-Δ-) indicate the percentage rejection (i.e., 100-percent permeability) of gamma-globulin and that of albumin, respectively.

Figure 4:
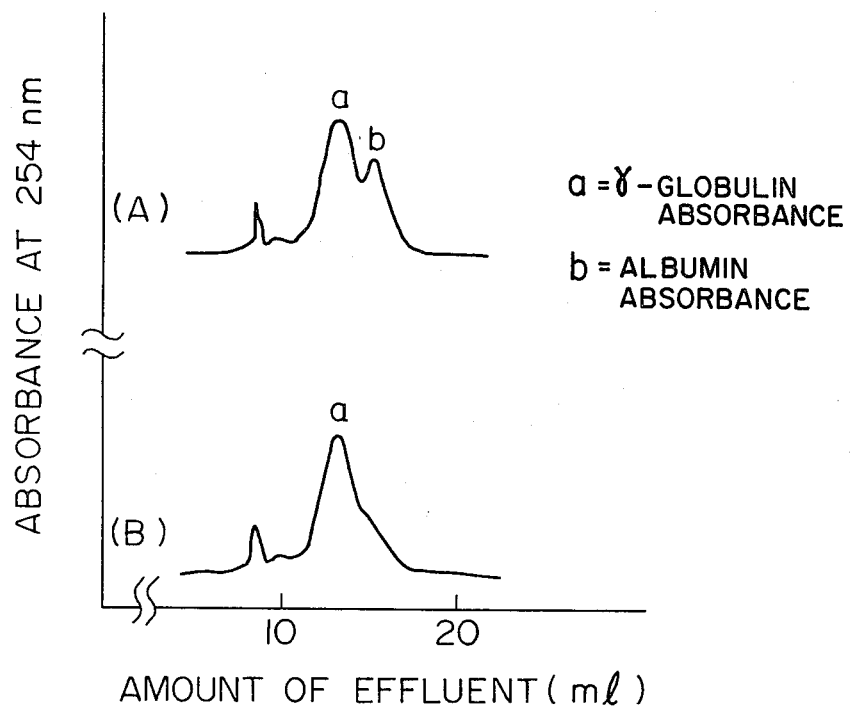
FIG. 4 shows chromatograms obtained by the liquid chromatography of a blood serum protein solution (A) used in another embodiment of the present invention and a protein solution (B) fractionated from the blood serum protein solution according to the present invention.
Figure 5:
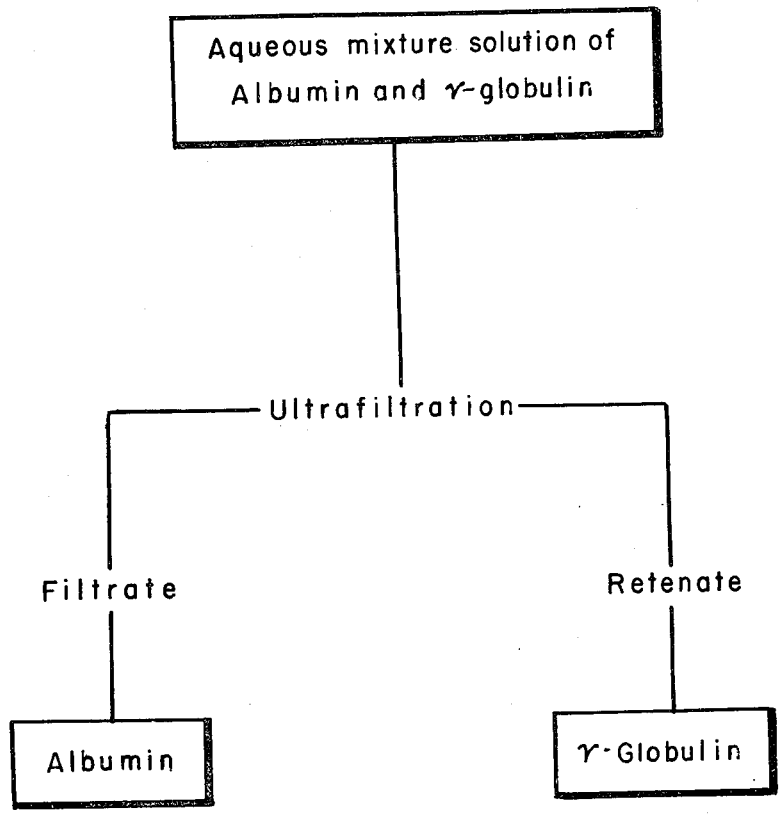
FIg. 5 is a flow chart illustrating the method of separating serum albumin and gamma-globulin from each other according to the present invention.

FIG. 4 (comparative example) illustrates chromatograms (A) and (B) which were obtained by the liquid chromatography of (i) a solution of a gamma-globulin fraction obtained by the precipitation fractionation of a human blood serum according to a polyethylene glycol precipitating method, and (ii) a retenate obtained when the solution (i) was ultrafiltered, respectively. In these chromatograms, the peaks a and b indicate the absorbance of gamma-globulin and albumin, respectively, as measured at a wavelength of 254 nm.

The present invention will now be described in detail with reference to the following Examples that by no means limit the scope of the invention.

In the Examples, liquid chromatograms of blood serum protein solutions were obtained by a liquid chromatograph manufactured and sold under the trade name of "HLC-802UR" by Toyo Soda Manufacturing Co., Ltd. A column G-3000SW (manufactured by Toyo Soda Manufacturing Co., Ltd.) was used as the column and a 1/15 M phosphate buffer solution having a pH of 6.8 was used as the eluent. The ultraviolet absorption at a wavelength of 254 nm was observed for detecting protein. The percentage rejection (R) referred to in the Examples is defined by the following formula:

$$R(\%) = \left(1 - \frac{\text{concentration in filtrate}}{\text{concentration in feed solution}}\right) \times 100$$

EXAMPLE 1

In 100 ml of N-methyl-2-pyrrolidone were dissolved 15 g of a polyether sulfone (trade name: "P-1700", manufactured by Union Carbide Corporation) having recurring units represented by the following formula:

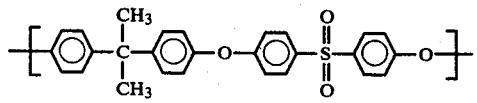

The resulting solution was cast in a thickness of about 200 microns on a polyethylene non-woven fabric, and then the non-woven fabric was dipped in water maintained at 15° C. to coagulate the polymer to obtain an asymmetric polyether sulfone membrane. The cut off molecular weight of this membrane was about 100,000. The percentage rejection of the membrane to a solution of bovine blood serum albumin in a 1/15 phosphate buffer solution having a pH value of 6.8 and an albumin concentration of 0.1% was about 80%.

A bovine blood serum from which macromolecular insoluble substances had been removed by centrifugal separation was diluted with pure water so that the volume was about 5 times the original volume, to form a solution having a protein concentration of about 1.5% by weight and a salt concentration of about 0.04 mole/l. Acetic acid was added to the solution to adjust the pH value to 4.1. Then, 50 ml of the solution was charged in an agitation type ultrafiltration cell provided with the above-mentioned polyether sulfone membrane of a circular figure having an effective diameter of 43 mm, and filtration was carried out under a pressure of 0.5 Kg/cm² until the volume of the solution in the cell was reduced to 10 ml. The feed solution and the obtained filtrate were analyzed by the liquid chromatography, and the obtained chromatograms are shown in FIG. 1, in which (A) shows the chromatogram of the feed solution and (B) shows the chromatogram of the filtrate. In these chromatograms, a indicates the peak of γ-globulin and b indicates the peak of albumin. It is seen that the γ-globulin was not substantially present in the filtrate. Then, 4.0 ml of an acetate buffer solution having a pH value of 4.1 and a salt concentration of 0.2 mole/l was added to the solution left in the cell the volume of which was 10 ml, and a pressure was applied again and the solution was condensed until the volume was reduced to 10 ml. This operation was repated 5 times as a whole. The solution finally retained on the membrane was analyzed by the liquid chromatography to obtain a chromatogram of FIG. 1-(C). It was seen that albumin was substantially removed.

EXAMPLE 2

A membrane of a material similar to that of the membrane used in Example 1, which had substantially the same capacity as that of the membrane of Example 1, was used, and the same bovine blood serum as used in Example 1 was treated. The pH value and the salt concentration were varied to determine influences of these factors on the permeability. Influences of the pH value (the salt concentration being set at 0.2 mole/l) are shown in FIG. 2, and influences of the salt concentration (the pH value being set at 4.1) are shown in FIG. 3. NaCl was used as the salt to be added. From the results shown in FIGS. 2 and 3, it will readily be understood that good separation results are obtained when the pH value is adjusted to 3.8 to 4.7, especially 3.8 to 4.3, and the salt concentration is not more than about 0.6 mole/l.

EXAMPLE 3

In 100 ml of dimethylacetamide was dissolved 16 g of an aromatic polyether sulfone having recurring units represented by the following formula:

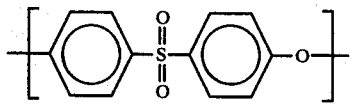

The solution was cast in a thickness of 200 microns on a polyethylene non-woven fabric, and the non-woven fabric was dipped in water to coagulate the cast solution and obtain an ultrafiltration membrane having a cut off molecular weight of about 10,000. The percentage rejection of the membrane to albumin in a 0.2% by weight solution buffered by a 1/15 M phosphate having a pH value of 6.8 was 55%.

A human blood serum was diluted with pure water so that the volume was 30 times the original volume to form a solution having a salt concentration of 0.01 mole/l. Acetic acid was added to the solution to adjust the pH value to 4.2. Then, the solution was subjected to the separation operation in the same manner as described in Example 1, wherein the above-mentioned aromatic polyether sulfone ultrafiltration membrane was used with all other conditions remaining substantially the same.

The albumin concentration in the filtrate was 30% as compared with that in the feed solution, and permeation of γ-globulin was not observed.

EXAMPLE 4 (COMPARATIVE EXAMPLE)

The separation operation and analysis were carried out in the same manner as described in Example 1 except that a commercially available membrane having a fractionation molecular weight of 100,000 and being composed of an acrylonitrile/vinyl chloride copolymer ("Diaflo XM-100" manufactured by Amicone Co. Ltd.) was used as the semipermeable membrane. All other conditions remained substantially the same as in Example 1.

The filtrate contained about 5% of the albumin contained in the feed solution. However, the flow rate of the filtrate was gradually decreased with the lapse of time.

EXAMPLE 5

A human blood serum was diluted with an acetate buffer solution having a pH value of 4.2 and a salt concentration of 0.2 mol/l so that the volume was 5 times the original volume to obtain a solution having a salt concentration of 0.2 mol/l. Then, the solution was filtered through a filter paper and a micro-filter having a pore diameter of 0.45 microns. The obtained blood serum solution was separated by using a commercially available membrane composed of the same material as that of the semipermeable membrane used in Example 1. The nominal cut off molecular weight of the membrane used was 100,000. More specifically, 50 ml of the blood serum solution was condensed under a pressure of 0.5 kg/cm² so that the volume was reduced to 1/5, and 40 ml of the above-buffer solution was added to the residual concentrate. This operation was repeated 6 times as a whole. The amounts of albumin and γ-globulin in the residual solution on the membrane were 8% and 98% of the original amounts, respectively.

EXAMPLE 6

5 g of a human blood serum second fraction obtained by the polyethylene glycol method [A. Polson et al., Biochem. Biophys. Acta., 82, 463 (1964)] were dissolved in one liter of an aqueous acetate buffer solution having a salt concentration of 0.2 mole/l and a pH value of 4.0. The obtained solution was analyzed by the liquid chromatography to obtain a chromatogram shown in FIG. 4-(A). The main component of the solution was γ-globulin (fraction a), but large quantities of macromolecules and albumin (fraction b) were contained.

A semipermeable membrane similar to that used in Example 3, having a diameter of 9 cm, was attached to a thin layer flow passage type cell ("TC-10" manufactured by Amicone Co. Ltd.), and a constant volume retention filtration of 500 ml of the above solution was carried out by using this cell. More specifically, a 0.5% acetic acid buffer solution having a salt concentration of 0.2 mole/l and a pH value of 4.0 was replenished in an amount corresponding to the amount of the filtrate so that 500 ml of the solution was always held in the cell.

After the operation was carried out continuously for about 5 hours, about 1.5 l of the filtrate was obtained. The solution remaining in the cell was analyzed by the liquid chromatography to obtain a chromatogram shown in FIG. 4-(B). It was seen that most of albumin was removed.

We claim:

1. A method of separating serum albumin and a serum γ-globulin from each other in a solution of a mixture thereof using a semipermeable membrane, said method comprising forcing the blood serum protein mixture solution through an ultrafiltration membrane having a cut off molecular weight of about 100,000 and composed of an aromatic polyether sulfone having recurring units represented by the following formula:

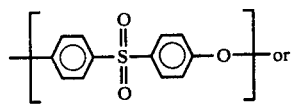

or

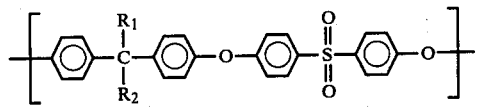

wherein $R_1$ and $R_2$ each stand for a hydrogen atom or an alkyl group having 1 to 2 carbon atoms,
while adjusting the total protein concentration and salt concentration in the mixture solution to not more than 4 g/dl and not more than 0.6 mole/l, respectively, and also adjusting the pH of the solution to a value of from about 3.8 to about 4.7.

2. A method according to claim 1, wherein the pH of the blood serum protein mixture solution is adjusted to a value of from 3.9 to 4.3.

3. A method according to claim 2, wherein the salt contained in the blood serum protein mixture solution is at least one salt selected from the group consisting of sodium chloride and other physiologically acceptable salts.

* * * * *